United States Patent
Dijkstra et al.

(10) Patent No.: US 10,258,001 B2
(45) Date of Patent: Apr. 16, 2019

(54) SPINACH PLANTS THAT ARE RESISTANT TO DOWNY MILDEW

(71) Applicant: NUNHEMS B.V., Nunhem (NL)

(72) Inventors: Jan Ane Dijkstra, Beegden (NL); Rob Raedts, Sevenum (NL)

(73) Assignee: NUNHEMS B.V., Nunhem (NL)

( * ) Notice: Subject to any disclaimer, the term of this patent is extended or adjusted under 35 U.S.C. 154(b) by 143 days.

(21) Appl. No.: 15/294,269

(22) Filed: Oct. 14, 2016

(65) Prior Publication Data

US 2017/0027126 A1 Feb. 2, 2017

Related U.S. Application Data

(63) Continuation-in-part of application No. 14/484,324, filed on Sep. 12, 2014, now Pat. No. 9,624,507.

(30) Foreign Application Priority Data

Sep. 13, 2013 (EP) ..................................... 13184388

(51) Int. Cl.
*A01H 5/12* (2018.01)
*A01H 6/02* (2018.01)
*C12Q 1/6895* (2018.01)
*A01H 1/04* (2006.01)

(52) U.S. Cl.
CPC ................ *A01H 5/12* (2013.01); *A01H 1/04* (2013.01); *A01H 6/028* (2018.05); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 7,935,866 B2 * | 5/2011 | Baerends | ................. | A01G 2/00 800/295 |
| 9,307,739 B2 * | 4/2016 | den Braber | .............. | A01H 5/12 |
| 2009/0300788 A1 * | 12/2009 | Baerends | ................. | A01H 5/12 800/268 |
| 2012/0222147 A1 | 8/2012 | Dijkstra | | |
| 2014/0065287 A1 * | 3/2014 | den Braber | .............. | A01H 5/12 426/615 |
| 2016/0177330 A1 * | 6/2016 | Dijkstra | ................... | A01H 1/04 800/265 |

FOREIGN PATENT DOCUMENTS

WO    WO 2013/064436 A1    5/2013

OTHER PUBLICATIONS

Hallavant & Ruas, Veget Hist Archaeobot 23(2):153-65 (2014).*
Correll et al., Eur J Plant Pathol 129:193-205 (2011).*
Irish et al., Plant Dis 91:1392-96 (2007).*
Merriam-Webster, "as" accessed Dec. 2, 2016.*
Irish et al., Irish et al., Phytopath 90(8):894-900 (2008).*
Brandenberger et al., Evaluation of Spinach Germplasm for Resistance to a New Race (Race 4) of *Peronospora farinosa* f. sp. *spinaciae*, Hort Science (1992), vol. 27, No. 20, pp. 1118-1119.
Corell et al., Guidelines for Spinach Downy Mildew: *Peronospora farinose* f. sp. *spinaciae* (Pfs), found on the website of the ISF (International Seed Federation) (2010).
Corell et al., Spinach: Better Management of Downy Mildew and White Rust Through Genomics, Eur J Plant Pathol (2011), vol. 129, pp. 193-205.
Extended European Search Report issued in corresponding Application No. EP13184388.0 dated Jan. 2, 2014.
Irish et al., Three New Races of the Spinach Downy Mildew Pathogen Identified by a Modified Set of Spinach Differentials, Plant Disease (2007), vol. 91, No. 11, pp. 1392-1396.
Kirk, Spinach Conference, Amsterdam, p. 26 (2011).
Nguyen et al., Effect of Plant Growth Regulator Combination and Culture Period on in vitro Regeneration of Spinach (*Spinacia oleracea* L.), Plant Biotechnology Reports (2013), vol. 7, No. 1, pp. 99-108.
Ranganathan, Differential Sets—*Peronospora farinose* f. sp. *spinaciae* (Pfs)-Spinach (2013), http://www.worldseed.org/cms/medias/file/TradeIssues/DiseasesResistance/Differentials/Spinach-downy.
Smith and Zahara, New Spinach Immune to Mildew, California Agriculture (1956).
Smith et al., Downy Mildew on Spinach, California Agriculture (1961).
Smith et al., Immunity to Race 2 of Spinach Downy Mildew, Phytopathology (1962).
The International Seed Federation, Differential Hosts (2013); http://www.worldseed.org/isf/differential_hosts.html.

* cited by examiner

*Primary Examiner* — Russell T Boggs
(74) *Attorney, Agent, or Firm* — Arent Fox LLP

(57) ABSTRACT

The present invention relates to the field of spinach breeding, in particular to a new dominant resistance gene, designated RPF11, which confers resistance against races 7 to 14 of *Peronospora farinosa* and to spinach plants comprising said gene.

22 Claims, No Drawings

Specification includes a Sequence Listing.

SEQUENCE LISTING

<160> NUMBER OF SEQ ID NOS: 2

<210> SEQ ID NO 1
<211> LENGTH: 201

```
<212> TYPE: DNA
<213> ORGANISM: Spinacia oleracea

<400> SEQUENCE: 1
attctaaatc aatttatttg tgtattcatt cttttgtatt aacagagact atttcaaagt      60
aagattattc attaattaat tattgcttct tacttccacc atttcaaaaa aaattgctaa     120
caattttaat tttgtcatta ttcatacacc aactttgacc atatatttta tggcatgtag     180
aaactcttac ttccaccatt t                                                201

<210> SEQ ID NO 2
<211> LENGTH: 201
<212> TYPE: DNA
<213> ORGANISM: Spinacia oleracea

<400> SEQUENCE: 2
tcattaattt cattttcttg tcgtatacga tttaaatcgt tttgtcatgt attgttagcc      60
ttttgtattg catatattgc ttgcattaac tttcacatta atgcggaaat tttaataaga     120
aactaaagta aaaacatgca taatattgct tgaaaactct ttgaaatatg attaacactt     180
ttgaaattaa tttgataact a                                                201
```

SPINACH PLANTS THAT ARE RESISTANT TO DOWNY MILDEW

CROSS-REFERENCE TO RELATED APPLICATIONS

This application is a continuation-in-part of U.S. application Ser. No. 14/484,324, filed on Sep. 12, 2014, which claims the benefit of European Application No. 13184388.0, filed Sep. 13, 2013, the contents of each which are hereby incorporated by reference in its entirety.

FIELD OF THE INVENTION

The invention relates to a new dominant resistance gene, designated RPF11, for use in breeding downy mildew resistant spinach plants. The present invention further relates to cultivated spinach (*Spinacia oleracea*) seeds, plants and plant parts (e.g. leaves) grown from the seeds, that are resistant to *Peronospora farinosa* f.sp. *spinaciae* (abbreviated herein as Pfs) due to the presence of RPF11 in their genome, as well as to progenies of the plants and propagation material for producing the plants.

BACKGROUND OF THE INVENTION

Spinach (*Spinacia oleracea*) has become an important vegetable crop in many parts of the world, with the top spinach producing county being China (>80% of global production), followed by USA, Japan and various European countries. Globally about 1 million ha of spinach are grown in Asia and about 35,000 ha in each of the EU, USA and Japan (see Correll et al., 2011, Eur J Plant Pathol 129: 193-205). Part of the increase in spinach demand is likely due to an increased health-consciousness of consumers and the beneficial properties of spinach. Spinach leaves are rich in beta-carotene, lutein, folic acid, vitamin C, calcium, iron and antioxidants. Especially the demand for fresh spinach has significantly increased over the last years.

Due to this increase in production over the last 10-15 years, incidence and severity of one of the most damaging pathogens of spinach, downy mildew of spinach, caused by races of the oomycete *Peronospora farinosa* f.sp. *spinaciae* (Pfs; synonym *P. effusa*) has increased concomitantly. Before 1990 only three races of Pfs were known, however between 1990 and 2010 ten new races were identified. The emergence of new races of Pfs makes this pathogen a major threat for spinach production globally and identifying new sources of resistance is therefore necessary.

Historically, Pfs race 1 (Pfs: 01 or Pfs 1) was first reported in 1824 and resistance to race 1 was identified later in two Iranian accessions (PI140467 and PI140464), and incorporated into commercial hybrid varieties, such as Califlay (Smith and Zahara, California Agriculture, July 1956). In 1958, race 2 appeared and a few years later a single dominant gene imparting resistance against both race 1 and race 2 was identified (Smith et al. 1961 and 1962). In 1976, race 3 appeared and again several years later resistance against race 3 was found. Race 4 was only identified in 1990, and Brandenberger et al. (1992) identified accessions CGN09546, of which 60% of individual plants were resistant, and SP1 82/87, of which 80% of individual plants were resistant. The rapid emergence of new races hereafter, lead to the identification of new resistance genes and their incorporation into commercial varieties, as indicated in Table 1 below (– means resistant reaction; + means susceptible reaction; (–) means reduced level of infection often referred to as field resistance, i.e. sparse sporulation on the tips of the cotyledons; +/– means undecided). These varieties are also used as host differentials for determining the race of isolates of Pfs (see document of the International Seed Federation, August 2013; world wide web at worldseed.org/isf/differential_hosts.html).

TABLE 1

| Variety | Pfs 1 | Pfs 2 | Pfs 3 | Pfs 4 | Pfs 5 | Pfs 6 | Pfs 7 | Pfs 8 | Pfs 9 | Pfs 10 | Pfs 11 | Pfs 12 | Pfs 13 | Pfs 14 |
|---|---|---|---|---|---|---|---|---|---|---|---|---|---|---|
| Viroflay | + | + | + | + | + | + | + | + | + | + | + | + | + | + |
| Resistoflay | – | – | + | + | + | + | + | + | + | + | + | + | + | + |
| Califlay | – | + | – | + | – | + | + | – | – | + | – | – | + | – |
| Clermont | – | – | – | – | + | + | + | + | + | + | + | + | + | + |
| Campania | – | – | – | – | – | + | – | + | + | + | – | + | +/– | + |
| Boeing (=Avenger in USA) | – | – | – | – | – | – | – | + | – | + | – | + | – | + |
| Lion | – | – | – | – | – | – | – | – | – | + | – | – | – | – |
| Lazio | – | – | – | – | – | – | – | – | – | – | + | + | + | + |
| Whale | – | – | – | (–) | – | (–) | (–) | – | – | + | – | – | + | (–) |

Commercial spinach varieties are mostly hybrids, produced by crossing a male and a female inbred line, although also some open pollinated varieties exist. The male and female parent line generally each carry a different resistance gene. For example, the hybrid variety Andromeda (Nunhems; see patent application US2012/0222147) is resistant against Pfs 1-12 and Pfs14. Resistance against Pfs 1, 3, 5, 8, 9, 11, 12 and 14 is conferred by a resistance gene from one parent, while resistance against Pfs 1-10 is conferred by a resistance gene from the other parent.

WO2013/064436 describes a dominant resistance gene, called R6, which confers resistance against Pfs1-6, 9, 11-14 (see Table 1 on page 19 of WO2013/064436; in 2011 the type strain UA4410 has been designated Pfs14 by the International Working Group on *Peronospora farinosa*, IWGP).

To achieve resistance against all known Pfs races (Pfs1-14) using the known resistance genes, one would for example need to combine the resistance genes of Lazio and Lion. To date, no single resistance gene is known, which confers resistance against all known Pfs races, or especially against Pfs races 7-14.

SUMMARY OF VARIOUS EMBODIMENTS OF THE INVENTION

It is, therefore, an object of the invention to provide a single dominant resistance gene, which confers resistance against at least Pfs races 7-14. In addition, the gene optionally also confers resistance against one or more (or all) of Pfs races 1-6. Optionally the gene also confers resistance against isolate UA4712. Thus, in one aspect, the resistance gene, designated RPF11, confers resistance against at least Pfs races 7-14, and optionally also against isolate UA4712 (Pfs race 15) and/or optionally against one or more of Pfs 1-6, especially at least against Pfs 1, 2, 5 and 6 or against at least Pfs 1, 2, 3, 5 and 6. In a further aspect, seeds, plants and plant parts of cultivated spinach comprising the new major resistance gene are provided. In one aspect, the RPF11 gene is located in between DNA markers SNP_01 and SNP_02. Thus, in one aspect, the seed, plant or plant part comprises in its genome a recombinant chromosome comprising an introgression fragment from a donor plant in its genome and wherein the introgression fragment carries the dominant RPF11 gene which is located between SNP_01 and SNP_02.

Also methods for identifying and/or selecting spinach plants or plant parts comprising the resistance gene are provided, as are methods for transferring the resistance gene from seeds deposited under accession number NCIMB 42158 into different spinach plant lines or varieties.

It is a further object to provide one or more markers, especially SNP_01 and SNP_02 and markers located in between SNP_01 and SNP_02, that can be used in the selection of plants or plant parts comprising the resistance gene, designated RPF11, which confers resistance against at least Pfs races 7-14, and optionally also against isolate UA4712 (Pfs race 15) and/or optionally against one or more of Pfs 1-6, especially at least against Pfs 1, 2, 5 and 6, especially at least against Pfs 1, 2, 3, 5 and 6. Also, methods for either generating or for identifying plants or plant parts comprising said resistance are provided. In some aspects, methods for selecting, identifying, and/or detecting the resistance gene, designated RPF11, comprise hybridizing one or more nucleic acid probes to a nucleic acid of a plant suspected of comprising RPF11, or amplifying a nucleic acid of a plant suspected of comprising RPF11 using one or more nucleic acid primers, are provided.

RPF11 is introgressed from wild spinach or a wild relative of spinach (the donor or resistance gene donor) into cultivated spinach (also referred to as the recurrent parent). In one aspect, a cultivated spinach plant or plant part is provided comprising an introgression fragment from a wild spinach or wild relative of spinach, wherein the introgression fragment comprises the dominant RPF11 gene, and wherein the RPF11 gene is located in between DNA markers SNP_01 and SNP_02.

Also provided is the use of the gene and molecular markers (especially Single Nucleotide Polymorphisms or SNPs, especially SNP_01 and/or SNP_02) flanking the gene for the identification of plants or plant parts comprising RPF11, and methods of using such markers in identifying or generating plants or plant parts comprising RPF11.

In one aspect, the cultivated spinach comprises a recombinant chromosome, said chromosome comprises the introgression fragment which comprises RPF11, wherein the recombinant chromosome is the chromosome on which SNP_01 and SNP_02 are located. In a further aspect, the remaining chromosomes of the genome of the plant are cultivated spinach chromosomes. In one embodiment, the introgression fragment comprising the RPF11 gene is on Linkage Group 1. Without limiting the invention, it is believed that Linkage Group 1 corresponds to Linkage Group P03 of Chan-Navarrete et al. (Euphytica 2016, 208: 621-636).

In one aspect, the RPF11 gene is the gene present in seeds deposited under accession number NCIMB42158 or in progeny thereof which retain the RPF11 gene in their genome, such as progeny which retain the RPF11 gene located in between SNP_01 and SNP_02. In one aspect, the progeny retain the SNP_01 and/or SNP_02 genotype of the donor, although the skilled person can also select plants which retain the RPF11 gene but lack SNP_01 and/or SNP_02 of the donor and thus comprise a shorter introgression fragment. Thus, in one aspect, the SNP genotype of SNP_01 and/or SNP_02 may also be the genotype of the recurrent parent, while the RPF11 gene is still present. A shorter introgression fragment can be identified by markers in between SNP_01 and SNP_02 which have a donor genotype and are linked to the RPF11 gene.

DETAILED DESCRIPTION OF EMBODIMENTS OF THE INVENTION

Definitions

The indefinite article "a" or "an" does not exclude the possibility that more than one of the element is present, unless the context clearly requires that there be one and only one of the elements. The indefinite article "a" or "an" thus usually means "at least one".

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"Spinach" or "cultivated spinach" or "cultivated *Spinacia oleracea*" refers herein to plants of the species *Spinacia oleracea* (or seeds from which the plants can be grown), and parts of such plants, bred by humans for food and having good agronomic characteristics. This includes any cultivated spinach, such as breeding lines (e.g. backcross lines, inbred lines), cultivars and varieties (open pollinated or hybrids). This includes any type of spinach, such as savoy, flat- or smooth-leaf spinach or semi-savoy types. Wild spinach (i.e. not cultivated spinach) or wild relatives of spinach, such as *Spinacia tetrandra* and *Spinazia turkestanica*, are not encompassed by this definition.

"Wild spinach" or "wild relatives of spinach" refer herein to the species *Spinacia tetrandra* and/or *Spinacia turkestanica*. These species are also referred to as the donor plants or donor species of the RPF11 gene, i.e., the introgression fragment comprising RPF11 is derived from such a wild spinach donor plant. The cultivated spinach into which the RPF11 gene of the donor is introgressed is referred to as the recurrent parent or cultivated parent.

As used herein, the term "plant" includes the seed (from which the plant can be grown), the whole plant or any parts such as plant organs (e.g., harvested or non-harvested leaves, etc.), plant cells, plant protoplasts, plant cell- or tissue cultures from which whole plants can be regenerated, propagating or non-propagating plant cells, plants cells which are not in tissue culture (but which are for example in vivo in a plant or plant part), plant callus, plant cell clumps, plant transplants, seedlings, plant cells that are intact in plants, plant clones or micro-propagations, or parts of plants (e.g., harvested tissues or organs), such as plant cuttings, vegetative propagations, embryos, pollen, ovules, flowers, leaves, heads, seeds (produced on the plant after self-fertilization or cross-fertilization), clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves. When "seeds of a plant" are referred to, these either refer to seeds from which the plant can be grown or to seeds produced on the plant, after self-fertilization or cross-fertilization.

"Somatic cells" and "reproductive cells" can be distinguished, whereby somatic cells are cells other than gametes (e.g. ovules and pollen), germ cells and gametocytes. Gametes, germ cells and gametocytes are "reproductive cells".

"Tissue Culture" or "cell culture" refers to an in vitro composition comprising isolated cells of the same or a different type or a collection of such cells organized into plant tissue. Tissue cultures and cell cultures of spinach, and regeneration of spinach plants therefrom, is well known and widely published (see, e.g. Nguyen et al., 2013, Plant Biotechnology Reports, Vol. 7 Issue 1, p. 99).

"Harvested plant material" refers herein to plant parts (e.g., leaves detached from the whole plant) which have been collected for further storage and/or further use.

"Harvested seeds" refers to seeds harvested from a line or variety, e.g., produced after self-fertilization or cross-fertilization and collected.

"Harvested leaves" as used herein refers to spinach leaves, i.e., the plant without the root system, for example substantially all (harvested) leaves.

"Progeny" or "progenies" or "descendants" as used herein refers to offspring, or the first and all further descendants derived from (obtainable from) (derivable from or obtained from) a plant of the invention that comprises (retains) the RPF11 resistance gene in homozygous or heterozygous form and/or the RPF11 resistance phenotype described herein. Progeny may be derived by regeneration of cell culture or tissue culture, or parts of a plant, or selfing of a plant, or by producing seeds of a plant. In further embodiments, progeny may also encompass spinach plants derived from crossing of at least one spinach plant with another spinach plant of the same or another variety or (breeding) line, and/or backcrossing, and/or inserting of a locus into a plant and/or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Also double haploid plants are progeny.

"Plant line" is for example a breeding line which can be used to develop one or more varieties. "Inbred line" or "inbred parent" is a line which has been developed by selfing for several generations and which can be used as a parent to produce an F1 hybrid variety.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"Hybrid" refers to the seeds harvested from crossing one plant line or variety with another plant line or variety, and the plants or plant parts grown from said seeds.

"F1 hybrid" plant (or F1 hybrid seed) is the generation obtained from crossing two non-isogenic inbred parent lines. Thus, F1 hybrid seeds are seeds from which F1 hybrid plants grow.

An "interspecific hybrid" refers to a hybrid produced from crossing a plant of one species, e.g. *S. oleracia*, with a plant of another species, e.g. *S. tetrandra* or *S. turkestanica*.

"Crossing" refers to the mating of two parent plants. Equally "Cross-pollination" refers to fertilization by the union of two gametes from different plants.

"Selfing" refers to the self-pollination of a plant, i.e. to the union of gametes from the same plant.

"Backcrossing" refers to a breeding method by which a (single) trait, such as Pfs resistance conferred by the RPF11 resistance gene, can be transferred from one genetic background (also referred to as "donor"; generally but not necessarily this is an inferior genetic background) into another genetic background (also referred to as "recurrent parent"; generally but not necessarily this is a superior genetic background). An offspring of a cross (e.g. an F1 plant obtained by crossing a wild spinach or wild relative of spinach with a cultivated spinach; or an F2 plant or F3 plant, etc., obtained from selfing the F1) is "backcrossed" to the parent with the superior genetic background, e.g. to the cultivated parent. After repeated backcrossing, the trait of the donor genetic background, e.g. the RPF11 gene, will have been incorporated into the recurrent genetic background. The terms "gene converted" or "conversion plant" or "single locus conversion" in this context refer to plants which are developed by backcrossing wherein essentially all of the desired morphological and/or physiological characteristics of the recurrent parent are recovered in addition to the one or more genes (e.g. the RPF11 resistance gene) transferred from the donor parent.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods), by which, for example, the RPF11-resistance gene can be obtained, identified, selected, and/or transferred.

"Regeneration" refers to the development of a plant from in vitro cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting off) leaf, pollen, embryo, cotyledon, hypocotyl, cells, protoplasts, meristematic cell, root, root tip, pistil, anther, flower, shoot tip, shoot, stem, fruit, and petiole. When a whole plant is regenerated by vegetative propagation, it is also referred to as a "vegetative propagation" or a "vegetatively propagated plant".

"Single locus converted (conversion) plant" refers to plants which are developed by plant breeding techniques comprising or consisting of backcrossing, wherein essentially all of the desired morphological and/or physiological characteristics of a spinach plant are recovered in addition to the characteristics of the single locus (e.g. the locus comprising the RPF11 gene) having been transferred into the plant via the backcrossing technique and/or by genetic transformation.

"Transgene" or "chimeric gene" refers to a genetic locus comprising a DNA sequence which has been introduced into the genome of a spinach plant by transformation. A plant comprising a transgene stably integrated into its genome is referred to as "transgenic plant".

"Pfs" or "*Peronospora farinosa*" or "downy mildew" refers to races of the oomycete *Peronospora farinosa* f.sp. *spinaciae*. Pfs1-Pfs14 refer to the officially recognized races, which can be differentiated on the differential hosts of spinach and which can be obtained from the Naktuinbouw, P.O. Box 40, 2370 AA Roelofarendsveen, The Netherlands, or via references provided by the ISF (International Seed Federation).

"Differential hosts" or "differentials" refers to the differential hosts of spinach for distinguishing Pfs races 1-14, which can be obtained from the Naktuinbouw, P.O. Box 40, 2370 AA Roelofarendsveen, The Netherlands, or via references provided by the ISF (International Seed Federation).

"UA4712" refers to a pathogenic isolate of Pfs which has by now been officially recognized as a new Pfs race, Pfs15. It was originally described by Correl and Koike, 2013, Race diversity and the biology of the spinach downy mildew pathogen, CLGRB Annual Report, Apr. 1, 2012 to Mar. 31, 2013. The UA4712 isolate was first identified in November 2012 in Imperial Valley, Calif., U.S. The isolate was evaluated for disease development in a test against a standard set of differential varieties, and as of September 2014 the International Working Group on *Peronospora* (IWGP) determined that the isolate was a new race, and named it Pfs 15 once it became clear that isolates with the same reaction pattern occurred in many locations (Plantum press release 2 Sep. 2014 "Denomination of Pfs: 15, a new race of downy mildew in spinach"). In this application, UA4712, Pfs 15, Pfs race 15 and Pfs: 15 will be used interchangeably.

A "Pfs resistant plant" or "downy mildew resistant plant" or a plant having "Pfs resistance" or a "Pfs resistant phenotype" refers to a spinach plant which is resistant against one or more pathogenic races (and pathogenic isolates) of Pfs, as determined in a qualitative resistance assay under controlled environmental conditions. In such a resistance assay, a plurality of plants (e.g. at least 2 replicates of at least 10 plants) of a genotype, are inoculated with a sporangial suspension of the race or isolate and incubated under suitable conditions. After a suitable incubation period (e.g. 7, 8, 9, 10, 11 or more days after inoculation), the plants are evaluated for symptoms. Susceptible controls should show sporulation at the time of symptom evaluation. Any plant showing sporulation on the cotyledons (and/or on the true leaf/leaves) is considered "susceptible", while any plant not showing any sporulation on the cotyledons (and/or on the true leaf/leaves) is considered "resistant". A plant genotype with more than 85% of the inoculated plants (preferably more than 95%) being classified as "resistant" plant is considered to a resistant against the race or isolate. In the test >85% of inoculated plants (preferably more than 95% of plants) of the susceptible control plant, such as cultivar Viroflay, should show sporulation. Suitable tests are described herein in the Examples, or in Irish et al. 2007 (Plant Disease Vol 91 No. 11, in Materials and Methods on page 1392-1394), or in Correll et al. 2010, "Guidelines for Spinach Downy Mildew: *Peronspora ferinosa* f.sp. *spinaciae* (Pfs)" found on the website of the ISF (International Seed Federation).

"RPF11" refers herein to a single, dominant Pfs resistance gene, which confers Pfs resistance (as defined above) against at least races 7-14, and optionally against UA4712 (Pfs race 15) (and optionally against new pathogenic isolates). In one embodiment, RPF11 refers to a resistance gene which confers resistance against at least races 7-14 and optionally further against one or more or all of races 1-6 (e.g. against at least races 1, 2, 5 and 6, or against at least races 1, 2, 3, 5 and 6), and/or optionally against UA4712 (and optionally against new pathogenic isolates).

The resistance against races 1, 2, 3, 5, 6, 7, 8, 9, 10, 11, 12, 13, 14 and 15 is conferred when the gene is in homozygous or heterozygous form.

The resistance phenotype is also referred to herein as the "Pfs resistance phenotype conferred by the RPF11 gene". In one embodiment, the RPF11"gene is located in between markers SNP_01 and SNP_02. The term "locus" (loci plural) means a specific place or places or a site on a chromosome where, for example, a gene (e.g. the RPF11 gene) or genetic marker is found. In spinach according to the invention, the resistance locus comprising the RPF11 gene is introgressed from a wild spinach or wild relative of spinach (i.e. the donor plant) into cultivated spinach (*S. oleracea*).

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Allelism test" refers to a genetic test whereby it can be tested whether a phenotype, such as Pfs resistance, seen in two plants, is determined by the same gene or by different genes. For example, the plants to be tested are crossed with each other, the F1 is selfed and the segregation of the phenotypes amongst the F2 progeny is determined. Other segregating populations can equally be made (e.g. backcross populations). The ratio of segregation of the phenotype indicates if the genes are allelic (alleles of the same gene) or non-allelic (different, independent genes).

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In spinach, wild spinach or wild relatives of spinach are used to introgress fragments of the wild genome into the genome of cultivated spinach. Such a spinach plant thus has a "genome of *Spinacia oleracea*", but comprises in the genome a fragment of a wild spinach or spinach relative, i.e. an introgression fragment of a donor plant. It is understood that the term "introgression fragment" never includes a whole chromosome, but only a part of a chromosome. The introgression fragment can be large, e.g. even half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1.5 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

"RPF11 comprising introgression fragment" or "RPF11 comprising introgression segment" or "RPF11 comprising introgression region" refers to the chromosome fragment comprising the RPF11 gene, whereby the RPF11 gene is located on the chromosome region in between SNP_01 and SNP_02. SNP_01 refers to nucleotide 101 of SEQ ID NO 1 or of a sequence comprising at least 90%, 95%, 97%, 98% or 99% sequence identity to SEQ ID NO: 1. SNP_02 refers to nucleotide 101 of SEQ ID NO 2 of a sequence comprising at least 90%, 95%, 97%, 98% or 99% sequence identity to SEQ ID NO: 2.

"SNP genotype" refers to the nucleotide found at the SNP location, i.e. at nucleotide position 101 of SEQ ID NO: 1 for SNP_01 and SEQ ID NO: 2 for SNP_02 (or at the corresponding position of a sequence comprising at least 90%, 95%, 97%, 98% or 99% sequence identity to SEQ ID NO: 1 or SEQ ID NO: 2, respectively). A "resistant SNP genotype" or a "donor SNP genotype" refers to an Adenine (A) being present at nucleotide 101 of the mentioned sequences. A "susceptible SNP genotype" or a "recurrent parent SNP genotype" or "cultivated SNP genotype" means that a Guanine (G), Cytosine (C) or Thymine (T) is present at nucleotide 101 of the mentioned sequences.

The same applies for markers located in between SNP_01 and SNP_02, and which are linked to the RPF11 gene. Such markers also have a donor genotype indicative of the introgression fragment or a recurrent parent genotype indicative of the cultivated spinach.

"Sequence identity" can be determined by alignment of two nucleotide sequences using global or local alignment algorithms. Sequences may then be referred to as "substantially identical" or "essentially similar" when they are optimally aligned by for example the programs GAP or BEST-FIT or the Emboss program "Needle" (using default parameters, see below) share at least a certain minimal percentage of sequence identity (defined further below). These programs use the Needleman and Wunsch global alignment algorithm to align two sequences over their entire length, maximizing the number of matches and minimizes the number of gaps. Generally, the default parameters are used, with a gap creation penalty=10 and gap extension penalty=0.5 (both for nucleotide and protein alignments). For nucleotides the default scoring matrix used is DNA-FULL. Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two nucleic acid sequences have "substantial sequence identity" if the percentage sequence identity is at least 90%, 95%, 96%, 97%, 98%, 99% or more (as determined by Emboss "needle" using default parameters, i.e. gap creation penalty=10, gap extension penalty=0.5, using scoring matrix DNAFULL for nucleic acids).

"Physical distance" between loci (e.g. between molecular markers and/or between phenotypic markers) on the same chromosome is the actual physical distance expressed in base pairs (bp), kilo base pairs (kb) or megabase pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

A genetic element, a locus, an introgression fragment or a gene or allele conferring a trait (such as resistance against Pfs) is said to be "obtainable from" or can be "obtained from" or "derivable from" or can be "derived from" or "as present in" or "as found in" a plant or seed if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like.

A "molecular marker" is a piece of DNA associated with a certain genomic or chromosomal location or single nucleotide polymorphism (SNP), which is found on the chromosome close to the gene of interest, preferably close to RPF11. Molecular markers can be used to identify a particular sequence of DNA, or a certain location in a genome or on a chromosome, or to identify an introgression fragment. When reference is made herein to one or more molecular markers being "detectable" by a molecular marker assay, this means of course that the plant or plant part comprises the one or more markers in its genome, as the marker would otherwise not be detectable. In one aspect, the marker is a Single Nucleotide Polymorphism (SNP), but other molecular markers such as RFLP, AFLP, RAPD, INDEL, DNA sequencing, etc. may equally be used. In one aspect, the marker SNP_01 at position 101 of SEQ ID NO: 1 (or of a sequence comprising substantial sequence identity to SEQ ID NO: 1) and/or SNP_02 at position 101 of SEQ ID NO 2 (or of a sequence comprising substantial sequence identity to SEQ ID NO: 2), or any molecular marker located in between SNP_01 and SNP_02 and being linked to the RPF11 gene can be used to select plants, plant tissues or plant parts comprising RPF11, and thus to select and/or generate Pfs resistance (as defined above) against at least races 7-14, and optionally against UA4712 (AKA Pfs race 15) (and optionally against new pathogenic isolates) or optionally further against one or more or all of races 1-6 (e.g. against at least races 1, 2, 5 and 6, or e.g. against at least races 1, 2, 3, 5 and 6).

"Flanking markers" are molecular markers located on the chromosome on either side of the RPF11 gene. SNP_01 and SNP_02 are flanking markers, i.e. the RPF11 gene is located in between SNP_01 and SNP_02.

Alternatively, other molecular markers can be developed which are linked to RPF11 and which lie in between SNP_01 and SNP_02 and these can then be used for identification or selection of the RPF11 gene, conferring Pfs resistance (as defined above) against at least races 7-14, and optionally against UA4712 (AKA Pfs race 15) (and optionally against new pathogenic isolates) or optionally further against one or more or all of races 1-6 (e.g. against at least races 1, 2, 5 and 6 or e.g. against at least races 1, 2, 3, 5 and 6). For example, fine-mapping can be carried out to find markers in the region between SNP_01 and SNP_02 which are linked even more closely to the RPF11 gene. Fine mapping involves making recombinant plants, which comprise recombinations in the region between SNP_01 and SNP_02 and analyzing whether these recombinant plants retain or lose the RPF11 gene. Thereby, the location of the RPF11 gene can be defined more precisely and markers in between SNP_01 and SNP_02 which are linked more closely to the gene can be identified. Alternatively, sequencing can be carried out to identify markers in-between SNP_01 and SNP_02 closely linked to the RPF11 gene or even within the gene.

The term "marker assay" or "genotyping assay" refers to an assay which can be used to determine the marker genotype, e.g. the SNP genotype. For example SNP markers can be detected using a KASP-assay (see world wide web at kpbioscience.co.uk) or other assays known to the skilled person.

"Marker assisted selection" or "MAS" is a process of using the presence of molecular markers, which are genetically and physically linked to a particular locus or to a particular chromosome region (e.g. introgression fragment), to select plants (e.g. progeny) for the presence of the specific locus or region (e.g. introgression fragment). For example SNP_01 and/or SNP_02, or any marker in between SNP_01 and SNP_02, may be used in MAS to select spinach plants or plant parts comprising the RPF11 gene.

When reference is made to a nucleic acid sequence (e.g. DNA or genomic DNA) having "substantial sequence identity to" a reference sequence or having a sequence identity of at least 80%, e.g. at least 85%, 90%, 92%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridization conditions. In another embodiment, the nucleic acid sequence comprises one or more mutations compared to the given nucleotide sequence but still can be identified using stringent hybridization conditions.

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100nt) are for example those which include at least one wash in 0.2×SSC at 63° C. for 20 min, or equivalent conditions. Stringent conditions for DNA-DNA hybridization (Southern blots using a probe of e.g. 100nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

Brief Description of Sequences

SEQ ID NO: 1 is the wild donor sequence for SNP_01 comprising an Adenine at nucleotide position 101, whereas the recurrent parent comprises a Guanine (G) at nucleotide 101.

SEQ ID NO: 2 is the wild donor sequence for SNP_02 comprising an Adenine at nucleotide position 101, whereas the recurrent parent comprises a Cytosine (C) at nucleotide 101.

Plants and Methods

The invention provides a spinach plant comprising resistance against at least *Peronospora farinosa* races 7-14, wherein said resistance is conferred by a single gene. The gene, designated herein RPF11 (for Resistance to *Peronospora Farinosa* 11) further optionally confers resistance against one or more of *Peronospora farinosa* races 1-6. In one aspect, the RPF11 gene, therefore, confers resistance against all currently known pathogenic Pfs races, races 1-14, when in homozygous or heterozygous form in the plant. In another aspect, the RPF11 gene confers at least resistance against pathogenic Pfs races 1 and 2 and 5 to 14 when in homozygous or heterozygous form in the plant. In yet another aspect, the RPF11 gene confers at least resistance against pathogenic Pfs races 7-14, when in homozygous or heterozygous form in the plant; and optionally also against one or more of races 1-6. Optionally, the resistance gene also confers resistance against one or more pathogenic isolates of Pfs, such as isolate UA4712 (Pfs race 15) or other isolates, including future isolates or races which develop in the field due to large scale uses of Pfs resistant spinach varieties. Thus, in another aspect, the RPF11 gene confers resistance against at least pathogenic Pfs races 7-14 and against UA4712, when in homozygous or heterozygous form in the plant.

The RPF11 gene is a single, dominant resistance gene, i.e. when a plant comprising RPF11 in homozygous form (such as a plant grown from seed deposited under accession number NCIMB 42158) is crossed with a susceptible plant, such as variety Viroflay, the F2 progeny will segregate in a 3 (resistant):1 (susceptible) ratio.

The RPF11 gene was found to be located in between the molecular markers SNP_01 and SNP_02. Therefore, in one aspect a spinach plant of the species *Spinacia oleracea* is provided comprising resistance against *Peronospora farinosa* races 7-14, wherein said resistance is conferred by a single dominant gene introgressed from *Spinacia tetrandra* or *Spinacia turkestanica*, which gene is located between SNP_01 at nucleotide 101 of SEQ ID NO: 1 or of a sequence comprising at least 95% sequence identity to SEQ ID NO: 1 and SNP_02 at nucleotide 101 of SEQ ID NO: 2 or of a sequence comprising at least 95% sequence identity to SEQ ID NO: 2.

In the mapping population, the SNP genotype of the donor was Adenine for SNP_01, rather than Guanine for the recurrent parent. The SNP genotype of the donor was Adenine for SNP_02, rather than Cytosine for the recurrent parent. Therefore, in one aspect, the nucleotide of SNP_01 and/or of SNP_02 is an Adenine. A diploid spinach plant homozygous for the introgression fragment comprising RPF11 therefore has, in one aspect, the SNP_01 genotype 'AA' (one Adenine on each chromosome) and/or the SNP_02 genotype of 'AA' (one Adenine on each chromosome). A plant heterozygous for the introgression fragment comprises the SNP_01 genotype 'AG' (or 'AC' or 'AT', depending on the recurrent parent background) and/or the SNP_02 genotype 'AC' (or 'AG' or 'AT' depending on the recurrent parent background).

In one embodiment, a spinach plant is encompassed of the species *Spinacia oleracea* comprising resistance against *Peronospora farinosa* races 7-14, wherein said resistance is conferred by a single dominant gene introgressed from *Spinacia tetrandra* or *Spinacia turkestanica*, which gene is located between SEQ ID NO: 1 or of a sequence comprising at least 95% sequence identity to SEQ ID NO: 1 and SEQ ID NO: 2 or of a sequence comprising at least 95% sequence identity to SEQ ID NO: 2.

The RPF11 gene can be identified in different wild spinach accessions, especially in accessions of the species *Spinacia tetrandra* or *Spinacia turkestanica*, and can be introgressed into cultivated spinach. To do this, the skilled person can screen wild spinach accessions for the presence of the resistance genotype for SNP_01 and/or SNP_02 and/or any marker in between SNP_01 and SNP_02. Alternatively, or in addition, the skilled person can test the Pfs resistance and optionally the inheritance (as single dominant gene) to determine if the wild accession contains RPF11. Finally, the skilled person can also do allelism tests or sequence the chromosome region between SNP_01 and SNP_02 to identify the presence of RPF11.

In one aspect, the RPF11 resistance gene is the gene present in plants grown from seeds, a representative sample of seeds having been deposited under accession number NCIMB 42158. However, as mentioned above, the RPF11 gene may also be derived from a different wild spinach or wild relative of spinach and introgressed into cultivated spinach.

The cultivated spinach plant according to the invention is, in one embodiment, a hybrid plant, especially an F1 hybrid made by crossing two inbred parent lines. The hybrid may comprise the introgression fragment comprising the RPF11 gene in homozygous or heterozygous form. In another embodiment, the cultivated spinach plant according to the invention is an inbred line. Such an inbred line may be a male or female line. It may comprise the introgression fragment in homozygous form. The cultivated spinach plant may be selected from the group consisting of: savoy, semi-savoy, flat- or smooth leaved.

In a specific aspect, the resistance against *Peronospora farinosa* is conferred by an introgression fragment from *Spinacia turkestanica*. The cultivated spinach plant therefore comprises the RPF11 gene located between SNP_01 and SNP_02, wherein the RPF11 gene is derived from *Spinacia turkestanica*.

The introgression fragment is, in one aspect, the fragment as found in spinach seeds, a representative sample of seeds having been deposited under accession number NCIMB 42158, or a sub-fragment thereof. A sub-fragment is a shorter fragment which still retains the RPF11 gene, but where on either side or on both sides of the gene a part of the introgression region has been removed by recombination. For example, the donor genotype of SNP_01 and/or SNP_02 may have been removed by recombination and is replaced by the cultivated spinach region of the chromosome. The skilled person can easily generate and identify plants comprising such sub-fragments of the introgression fragment of seeds deposited under NCIMB42158. The skilled person can, for example, cross a plant grown from the deposited seeds with another cultivated spinach plant (e.g. a plant susceptible to one or more of Pfs races 7-15), and then self the F1 progeny to produce an F2 population and identify recombinants (cross-over events) having occurred in the region between SNP_01 and SNP_02. Such sub-fragments contain donor markers, i.e. markers which lie in between SNP_01 and SNP_02.

The single, dominant RPF11 resistance gene, which is effective against all, or almost all, know pathogenic races, is of great advantage in generating resistant spinach varieties. To date, resistance genes with complementary resistance phenotypes have been stacked to provide resistance against several races. For example, the F1 hybrid variety *Andromeda* is a stack of two resistance genes, one inherited from the female parent and one from the male parent line. Therefore, the products described herein (e.g., plants, plant parts, progeny plants, etc.) provide a significant improvement over prior plants.

A representative sample of seeds of a spinach line comprising the RPF11 gene in homozygous form has been deposited under Accession number NCIMB 42158.

In one aspect of the invention, a spinach plant comprising the RPF11 resistance gene is obtainable by (or obtained by, or derivable from, or derived from) crossing a spinach plant grown from seeds deposited under accession number NCIMB 42158, with another spinach plant, for example with a spinach plant lacking Pfs resistance genes (a susceptible plant) or with a spinach plant comprising one or more different Pfs resistance genes. Thus, in one aspect, a spinach plant comprising resistance against at least *Peronospora far/nose* races 7-14 is provided wherein the resistance is conferred by a single dominant gene, called RPF11, wherein the RPF11 gene is the gene as present in seeds deposited under NCIMB41258 or progeny thereof.

In one embodiment of the invention, the RPF11 gene is, therefore, the gene as found in plants (or plant parts) grown from seeds deposited under accession number NCIMB 42158 or in progeny of such plants, such as plants obtained by selfing NCIMB 42158 or by crossing NCIMB 42158 with another spinach plant to obtain progeny and by retaining the resistance gene in the progeny (e.g. using phenotypic and/or molecular methods to identify or select progeny containing the RPF11 gene). Preferably, said molecular methods includes the use of molecular markers SNP_01 and/or SNP_02 and/or any molecular marker located in between SNP_01 and SNP_02 and linked to the introgressed RPF11 gene.

Therefore, in one embodiment of the invention, a spinach plant is provided comprising resistance against *Peronospora farinosa* races 7-14, wherein said resistance is conferred by a single gene, wherein said gene is the gene as found in (or as obtainable from) seeds deposited under accession number NCIMB42158, e.g. by crossing a plant grown from seeds of accession number NCIMB42158 with another spinach plant. In one aspect the (dominant) gene is in homozygous or heterozygous form. In another aspect, the single gene is detectable by the donor genotype of SNP_01 and/or SNP_02 and/or any molecular marker located in between SNP_01 and SNP_02 and linked to the introgressed RPF11 gene.

Thus, in one aspect a method for screening, and optionally selecting, spinach seeds, plants or plant parts or DNA from such seeds, plants or plant parts for the presence of one or more markers linked to the RPF11 gene is provided, said method comprising determining the presence of:
a) a Adenine (A) at nucleotide 101 of SEQ ID NO: 1 (SNP_01) or of a sequence comprising at least 90%, 91%, 92%, 93%, 94%, 95%, 96%, 97%, 98% or 99% sequence identity to SEQ ID NO: 1; and/or
b) a Adenine (A) at nucleotide 101 of SEQ ID NO: 2 (SNP_02) or of a sequence comprising at least 90%, 91%, 92%, 93%, 94%, 95%, 96%, 97%, 98% or 99% sequence identity to SEQ ID NO: 2; and/or
c) a molecular marker in between SNP_01 and SNP_02 and which is physically linked to the RPF11 gene.

In other aspects, the RPF11 gene is detectable using one or more nucleic acid probes, nucleic acid primers, or a combination thereof.

Thus, in one aspect the RPF11 gene is detectable by one or more nucleic acid probes, which hybridize to genomic DNA obtained from a plant or plant part comprising the RPF11 gene using stringent hybridization conditions described herein.

A nucleic acid probe may for example be a DNA molecule which comprises SEQ ID NO: 1 (or which comprises a sequence comprising at least 90%, 95%, 97%, 98% or more sequence identity to SEQ ID NO: 1) or its complement, or SEQ ID NO: 2 (or which comprises a sequence comprising at least 90%, 95%, 97%, 98% or more sequence identity to SEQ ID NO: 2) or its complement; or a DNA molecule obtained from the genomic sequence between SEQ ID NO: 1 (or a sequence comprising at least 90%, 95%, 97%, 98% or more sequence identity to SEQ ID NO: 1) and SEQ ID NO: 2 (or a sequence comprising at least 90%, 95%, 97%, 98% or more sequence identity to SEQ ID NO: 2).

In another aspect the RPF11 gene is detectable by one or more nucleic acid primers, which amplify genomic DNA linked to the RPF11 gene. For example, the primers may amplify a nucleic acid molecule comprising SNP_01 or SNP_02, or comprising a molecular marker in between SNP_01 and SNP_02. Suitable primers are for example the 70 to 100 bp upstream and 70 to 100 bp downstream of the marker (e.g. SNP_01 or SNP_02) can be selected to design a forward and a reverse primer, which amplify the marker. The primers can be used e.g. for SNP genotyping, e.g. in a KASP-assay for detecting the SNP genotype for SNP_01 and/or SNP_02.

In any of the probe and/or primer embodiments, or methods of the using the same, the probe and/or primer may comprise a label (e.g., fluorescent label).

In fact, the RPF11 gene (and the Pfs resistance phenotype conferred by the gene), can be transferred from the seeds deposited under NCIMB 42158, or from progeny of said seeds, into any spinach line or variety by traditional breeding techniques and can confer race 7-14 resistance, optionally further one or more or all of race 1-6 resistance (e.g. at least race 1, 2, 5 and 6 or e.g. against at least races 1, 2, 3, 5 and 6), and/or UA4712 (fs race 15) resistance (and optionally resistance against new pathogenic isolates) onto another spinach plant. Thus, for example, a spinach plant of the invention can be used as male or female parent in a cross with another spinach plant, and progeny, such as F1, F2, F3, or further generations of selfing and/or backcross progeny (e.g. BC1, BC2, BC1S1, BC2S1, BC1S2, etc.) can be identified and selected, whereby the progeny comprise the same Pfs resistance phenotype as the initial plant of the invention. Selection of progeny for the presence of the RPF11 gene (and the Pfs resistance phenotype conferred by the gene) can, therefore, be carried out using a disease resistance assay as described herein, whereby resistance against one or more (or all) of the Pfs races is tested in the progeny.

It is not always necessary to test progeny plants for resistance against all the Pfs races, as the transfer of resistance against one race is indicative of the transfer of the gene and the resistance against the other races is automatically transferred with the gene. Thus, if the second parent in the cross lacks resistance against a particular Pfs race, then selection of progeny which are resistant against that race is sufficient to indicate the transfer of the RPF11 gene.

Therefore, in one aspect of the invention, a spinach is provided comprising resistance against at least *Peronospora farinosa* races 7-14, optionally further comprising resistance against one or more of races 1-6 and/or optionally further comprising resistance against isolate UA4712 (Pfs race 15) and optionally new pathogenic isolates. Optionally, the RPF11 gene also provides resistance against one or more races selected from the group consisting of race 1, 2, 3, 4, 5 and 6, especially at least races 1, 2, 5 and 6, especially against races 1, 2, 3, 5 and 6. In a further embodiment, the spinach plant comprises resistance against at least Pfs races 7-14 and UA4712 and optionally further new pathogenic isolates. In yet a different embodiment, the spinach plant comprises resistance against at least one or more or all Pfs races selected from the group of 1, 2, 3, 4, 5 and 6 (for example at least against 1, 2, 5 and 6 or e.g. against at least races 1, 2, 3, 5 and 6), and additionally against 7 to 14 and UA4712 and optionally further new pathogenic isolates. When reference is made elsewhere herein to 'resistance against Pfs races 7-14', or to 'resistance against at least races Pfs 7-14', it is understood that the other resistances conferred by the RPF11 gene (as described above) are also encompassed in these or different embodiments.

Whether a spinach plant genotype (i.e. a spinach line or variety) comprises resistance against one or more Pfs races or isolates can be tested using qualitative disease resistance assays under controlled environment conditions. Different protocols of such assays exist and can be used by the person skilled in the art. In short, seedlings of a plurality of plants of the plant genotype to be tested (e.g. at least 6, 7, 8, 9, 10, 11, 12, 13, 14, 15, 16, 17, 18, 19, 20, or more) are inoculated with inoculum of the Pfs race and the seedlings are incubated under conditions which are favorable to the pathogen. Several days after incubation, the plants are assessed for infection symptoms, especially sporulation on the cotyledons and/or leaves (e.g. first true leaf), and each plant is categorized as "resistant" (showing no signs of sporulation) or "susceptible" (showing sporulation). If a certain percentage of all plants of a genotype are classified as "resistant", e.g. more than about 85%, 90%, 95%, 98%, 99% (or even 100%), then the spinach plant genotype is resistant to the race tested. Obviously, also one or more control plants (e.g. a susceptible line or variety, a resistant line or variety) should be included in the assay using the same treatment(s) and environmental conditions, to ensure that the assay works as expected.

Alternatively, or in addition to the phenotypic assay, selection or identification of a spinach plant (e.g. a progeny plant) comprising the RPF11 gene of the invention may be achieved by detecting one or more molecular markers linked to the RPF11 gene or locus, such as SNP_01 and/or SNP_02 or a marker located in between SNP_01 and SNP_02 and linked to the introgressed RPF11 gene.

In another embodiment, a spinach plant or a progeny of a spinach plant can be selected for the presence of the RPF11 gene by detecting whether the donor genotype for SNP_01 and/or SNP_02 and/or a marker located in between SNP_01 and SNP_02 and linked to the introgressed RPF11 gene.

A molecular marker between SNP_01 and SNP_02 linked to the RPF11 gene is a marker (e.g. single nucleotide, SNP, or a sequence of nucleotides) present on the introgression fragment and that has a different genotype than the cultivated *S. oleracea* genotype (i.e. is polymorphic with the cultivated spinach). In other words, a marker located in between SNP_01 and SNP_02 has a donor genotype, which is the genotype of the wild spinach or wild relative of spinach.

The molecular markers described herein may be detected according to a standard method. For example SNP markers can easily be detected using a KASP-assay (see world wide web at kpbioscience.co.uk) or other SNP genotyping assays. For example, a TaqMan SNP genotyping assay, a High Resolution Melting (HRM) assay, SNP-genotyping arrays (e.g. Fluidigm, Illumina, etc.) or DNA sequencing may equally be used. For developing a KASP-assay, for example 100 base pairs upstream and 100 base pairs downstream of the SNP can be selected and two allele-specific forward primers and one allele specific reverse primer can be designed. See e.g. Allen et al. 2011, Plant Biotechnology J. 9, 1086-1099, especially p097-1098 for KASP assay method. So for example a KASP-assay can be developed easily for SEQ ID NO 1 and/or SEQ ID NO 2 in order to detect the SNP genotype for SNP_01 and/or SNP_02.

In one embodiment of the invention, the spinach plant is an inbred line, especially an inbred line which can be used as a parent for F1 hybrid seed production. In another embodiment of the invention, the spinach plant is a hybrid, especially an F1 hybrid. An F1 hybrid may be generated by crossing a first inbred parent line which comprises the RPF11 gene, preferably in homozygous form, with a second inbred parent line. In one aspect, the first inbred parent line may be a line developed from using seeds deposited under NCIMB 42158 or from progeny of plants grown from these seeds, whereby the progeny retain the Pfs resistance phenotype (and the RPF11 gene).

In one aspect, the inbred line is a spinach plant of the species *Spinacia oleracea* comprising resistance against *Peronospora farinosa* races 7-14, wherein said resistance is conferred by a single dominant gene introgressed from *Spinacia tetrandra* or *Spinacia turkestanica*, which gene is located between SNP_01 at nucleotide 101 of SEQ ID NO: 1 or of a sequence comprising at least 95% sequence identity to SEQ ID NO: 1 and SNP_02 at nucleotide 101 of SEQ ID NO: 2 or of a sequence comprising at least 95% sequence identity to SEQ ID NO: 2.

The second inbred parent line may be any spinach line, i.e. it may completely lack Pfs resistance, or it may comprise a different Pfs resistance gene (and different resistance phenotype) or it may also comprise the RPF11 gene.

As the RPF11 gene is dominant, a hybrid spinach plant comprising only one copy of the RPF11 gene will show the resistance phenotype against Pfs races 1, 2, 3, 5, 6, 7-14 and 15 conferred by the gene.

As mentioned, the spinach plant according to the invention may be any type of spinach, as the RPF11 gene can be easily transferred into any spinach line or variety. For example, the spinach plant may be a savoy type, a semi-savoy type or flat- or smooth leaved spinach. In other words, the RPF11 gene can be introduced into any other spinach plant by introgression from a plant grown from seeds of which a representative sample was deposited under NCIMB 42158, or any spinach plant derived therefrom and comprising the RPF11 gene. The deposited seeds are therefore a source of the RPF11 resistance gene of the invention, as are spinach plants not directly obtained from the deposit, but for example indirectly obtained (e.g. later released commercial varieties) and which contain the RPF11 gene of the invention. Other sources of the RPF11 gene may be identified, e.g. in wild spinach or wild relatives of spinach and e.g. an allelism test may be used to determine whether another dominant gene, conferring the same Pfs resistance phenotype as the plant of the invention (or as progeny thereof), is the same gene or a different gene. Alternative methods to determine whether another gene is the same gene include the development of molecular markers linked to the RPF11 gene of the invention, such as SNP_01 and SNP_02 or any marker in between SNP_01 and SNP_02 linked to RPF11, and analyzing whether the markers, especially the donor genotype, also occur in plants comprising the other gene.

The RPF11 gene was identified in wild material from a genebank and was introduced through backcrossing into *S. oleracea*. In one aspect, therefore, a spinach plant is provided comprising resistance against at least Pfs races 7-14, optionally further against one or more of races 1 to 6, and/or optionally further against UA4712 (Pfs race 15) and/or new pathogenic isolates, wherein said resistance against *Peronospora farinosa* is conferred by an introgression fragment from wild spinach or from a wild relative of spinach, wherein the wild relative is selected from *Spinacia tetranda* and *Spinacia turkestanica*.

In one embodiment, the introgression fragment is the fragment as found in (and as obtainable from; or obtained from; or derivable from; or derived from) spinach seeds, a representative sample of seeds having been deposited under accession number NCIMB 42158. The fragment can be identified by various methods, such as chromosome painting or sequencing the spinach genome and identifying chromosome parts which are introgressions from wild spinach or wild relatives of spinach. The fragment can also be identified by one or more molecular markers (e.g. SNP markers, AFLP markers, RFLP markers, etc.), especially molecular markers which are polymorphic between cultivated spinach and the wild introgression fragment. Thus, in one aspect, the plant comprising the RPF11 gene as found in NCIMB 42158 comprises the same RPF11 markers or genomic gene sequence or introgression fragment as found in NCIMB42158 (or in progeny thereof). In one embodiment, the introgression fragment can be identified by determining whether the donor genotype for SNP_01 and/or SNP_02 and/or any marker located in between SNP_01 and SNP_02 and being linked to RPF11 is present.

In another embodiment, the introgression fragment is derived from the fragment as found in spinach seeds, a representative sample of seeds having been deposited under accession number NCIMB 42158, whereby the introgression fragment is shorter but retains the RPF11 gene (and the Pfs resistance phenotype conferred by the gene). Spinach plants comprising such shorter introgression fragments can be generated by crossing a plant of the invention with another spinach plant and selecting recombinant progeny which retain the resistance phenotype conferred by the RPF11 gene, but which contain a shorter introgression fragment. Additionally, SNP_01 and/or SNP_02 and/or any marker located in between SNP_01 and SNP_02 and being linked to PRF11 can be used in identifying recombinant plants comprising a shorter introgression fragment or sub-fragment of the fragment found in NCIMB42158.

Also provided is a method for generating a spinach plant comprising resistance against *Peronospora farinosa* races 7-14 comprises the steps of:
- a) crossing a first spinach plant of the species *Spinacia oleracea* with a second spinach plant which second spinach plant is susceptible against one or more of *Peronospora far/nose* races 7 to 14, wherein the first a spinach plant comprising resistance against *Peronospora farinosa* races 7-14, wherein said resistance is conferred by a single dominant gene introgressed from *Spinacia tetrandra* or *Spinacia turkestanica*, which gene is located between SNP_01 at nucleotide 101 of SEQ ID NO: 1 or of a sequence comprising at least 95% sequence identity to SEQ ID NO: 1 and SNP_02 at nucleotide 101 of SEQ ID NO: 2 or of a sequence comprising at least 95% sequence identity to SEQ ID NO: 2;
- b) selfing a plant grown from progeny of said crossing one or more times to produce a further generation selfing progeny and/or backcrossing a plant grown from progeny of said crossing or grown from the further generation selfing progeny with a spinach plant is susceptible against one or more of *Peronospora far/nose* races 7 to 14; and
- c) identifying a spinach plant among the progeny plants of step b) that comprises the a single dominant gene of the first parent plant of step a).

In one aspect, the genotype of SNP_01 and/or SNP_02 and/or a molecular marker located in between SNP_01 and SNP_02 (and being linked to the RPF11 gene) is used to identify a plant in step c).

In one aspect, the nucleotide of SNP_01 and/or of SNP_02 is an Adenine, i.e. the donor nucleotide. Therefore in one aspect the plant comprises an introgression fragment which comprises the donor SNP_01 and/or the donor SNP_02 genotype.

In another aspect, the genotype for SNP_01 and SNP_02 is the recurrent parent genotype and the introgression fragment is a fragment in between SNP_01 and SNP_02. Such a shorter introgression fragment comprises a donor genotype for one or more markers located in between SNP_01 and SNP_02.

A plant produced by the above method is also an embodiment of the invention.

In another aspect, a method is provided for generating a spinach plant comprising resistance against at least Pfs races 7-14, optionally further against one or more of races 1 to 6 (such as at least races 1, 2, 5 and 6 or against at least 1, 2, 3, 5 and 6), and/or optionally against UA4712, comprising the steps of:
- a) providing a spinach plant comprising resistance against at least Pfs races 7-14, optionally further against one or more of races 1-6, and/or optionally against UA4712;
- b) crossing said spinach plant with another spinach plant to produce F1 seeds;
- c) optionally selfing the plants grown from F1 seeds one or more times to produce F2, F3 or further generation selfing progeny;
- d) identifying (or selecting) spinach plants grown from F1, F2, F3 or further generation selfing progeny which have resistance against at least Pfs races 7-14, optionally further against one or more of races 1-6, and/or optionally against UA4712;
- e) optionally crossing said identified (or selected) F1, F2, F3 progeny or further generation selfing progeny to the spinach plant of step b), to produce a backcross progeny; and
- f) optionally selecting backcross progeny comprising resistance against at least Pfs races 7-14, optionally further against one or more of races 1-6, and/or optionally against UA4712.

In another embodiment, a method for generating a spinach plant comprising resistance against at least *Peronospora farinosa* races 7-14 (optionally further against one or more of races 1-6 such as at least races 1, 2, 5 and 6 or against at least 1, 2, 3, 5 and 6, and/or optionally against UA4712) is provided comprises the steps of:
- a) providing a spinach plant comprising an introgression fragment obtainable from (or as in) accession NCIMB 42158, which introgression fragment confers resistance against at least *Peronospora farinosa* races 7-14 (optionally further against one or more of races 1-6, and/or optionally against UA4712);
- b) crossing said spinach plant with another spinach plant, for example with a spinach plant which is susceptible against one or more of *Peronospora farinosa* races 7-14, to produce F1 seeds;
- c) optionally selfing the plants grown from F1 seeds one or more times to produce F2, F3 or further generation selfing progeny;
- d) identifying spinach plants grown from F1, F2, F3 or further generation selfing progeny which have resistance against at least *Peronospora farinosa* races 7-14 (optionally further against one or more of races 1-6, and/or optionally against UA4712) and/or which comprise the introgression fragment or a resistance-conferring part of the introgression fragment;
- e) optionally crossing said identified F1 progeny or selfing progeny to the spinach plant of step b), to produce a backcross progeny; and
- f) optionally selecting backcross progeny which comprises resistance against at least *Peronospora farinosa* races 7-14 (optionally further against one or more of races 1-6, and/or optionally against UA4712) and/or which comprise the introgression fragment or a resistance-conferring part of the introgression fragment.

Regarding the above methods, the following is encompassed herein.

In one aspect, the plant of a) comprises the RPF11 gene as found in seeds deposited under accession number NCIMB 42158. The spinach plant may be the plant grown from the seeds of the deposit or any spinach plant made using, or having used, the seed deposit and which retains the Pfs resistance phenotype (and the gene conferring it). This includes commercial spinach varieties which were made using the seed deposit. Thus, the spinach plant of a) comprises the RPF11 gene according to the invention, e.g. as found in (or as obtainable from; obtained from; derivable from; derived from) NCIMB 42158. The plant in a) may therefore be a plant grown from seeds, a representative sample of which has been deposited under NCIMB42158 (comprising RPF11 in homozygous form) or from progeny of such seeds which retain the RPF11 gene and phenotype.

Selections (or identification) in step d) and/or f) may be made based on the phenotype (i.e. using a Pfs resistance assay) and/or based on molecular methods, such as detection of molecular markers linked to the RPF11 gene or locus, or other methods such as sequencing. Suitable markers are SNP_01, SNP_02 and other markers in between SNP_01 and SNP_02, as described.

In the methods above, the spinach plant of step (a) preferably comprises the RPF11 gene (i.e. the introgression fragment comprising the RPF11 gene) in homozygous form.

In step b) the spinach plant is, in one aspect, crossed with a spinach plant which is susceptible against at least one of the Pfs races against which the plant of a) is resistant. If the second parent in b) is a spinach plant which is susceptible against at least one of the Pfs races against which the plant of a) is resistant, then the selection in step (d) and/or (f) may be based on selecting plants which now have resistance against that race.

Steps e) and f) may be repeated one or more times.

In the above methods, plants can also be selected and/or identified which retain the Pfs resistance phenotype conferred by the RPF11 gene, but which have a smaller introgression fragment. This can have advantages, as negative traits coupled to the wild introgression fragment can thereby be removed. Initial introgression fragments from wild sources can be quite large, e.g. 20 Mb or 30 Mb. It is therefore preferred to reduce the size of the introgression fragment by recombination and to select plants comprising smaller introgression fragments, but which retain the resistance-conferring part. So, spinach with all sizes of introgression fragments originating from (or derived from; or derivable from; or obtained from; or obtainable from) seeds deposited under accession number NCIMB 42158 are included herein, as long as the Pfs resistance conferring part (i.e. the RPF11 gene) is retained in the spinach plant. As mentioned, the presence can be tested/selected phenotypically and/or using molecular methods known in the art.

Also, a method for identifying, detecting or generating a cultivated spinach plant or plant part comprising the RPF11 gene is provided, optionally wherein said introgression fragment is as found in NCIMB 42158 or a smaller fragment derived therefrom, comprising:
  a) providing a cultivated spinach plant or plant part or DNA of such plant or plant part,
  b) screening said plant, plant part or DNA using a molecular marker assay which detects at least one SNP marker selected from the group consisting of:
SNP_01, SNP_02, a marker in between SNP_01 and SNP_02 linked to the RPF11 gene, or a combination thereof; and
  c) identifying, selecting, and/or generating a plant comprising the donor genotype for: SNP_01, SNP_02, a marker in between SNP_01 and SNP_02 linked to the RPF11 gene, or a combination thereof.

In yet another aspect, a method for detecting whether a cultivated spinach plant comprises an introgression fragment conferring resistance against at least Pfs races 7-14, and optionally also against isolate UA4712 (Pfs race 15) and/or optionally against one or more of Pfs 1-6 is provided, said method comprising:
  a) providing cultivated spinach plant or a plant part; and
  b) screening said plant or said plant part (or DNA obtained from said plant or plant part) using a molecular marker assay which detects at least one SNP marker selected from the group consisting of: SNP_01, SNP_02, a marker in between SNP_01 and SNP_02 linked to the RPF11 gene, or a combination thereof.

Also, plants obtainable or obtained by any of the above methods are embodiments of the invention.

The plants according to the invention may be any cultivated spinach, e.g. savoy, semi-savoy, flat- or smooth leaved spinach. They may be inbred lines, F1 hybrids, double haploids, transgenic plants, mutant plants, a single locus converted plant comprising the RPF11 gene, etc.

Plants of the invention can be used to generate progeny, which have or retain the Pfs resistance phenotype as obtainable from (as present in; as derivable from; as obtained or derived from) seeds deposited under NCIMB 42158. To generate progeny, a spinach according to the invention can be selfed and/or crossed one or more times with another spinach plant and seeds can be collected. The presence of the RPF11 gene in the progeny plants can be determined (i.e. progeny plants comprising the RPF11 gene can be identified/selected) by the Pfs resistance phenotype and/or molecular methods, such as molecular markers (e.g. SNP markers) closely linked to the RPF11 gene or locus.

Also seeds from which the plants of the invention can be grown are provided.

In one embodiment, the use of a spinach plant, of which representative seeds have been deposited under accession number NCIMB 42158, or progeny thereof (e.g. obtained by selfing), for generating a spinach plant comprising Pfs resistance against at least *Peronospora farinosa* races 7-14 (optionally further against one or more of races 1-6, and/or optionally against UA4712) is provided.

In another embodiment, the use of a spinach plant comprising resistance against at least *Peronospora farinosa* races 7-14 conferred by an introgression fragment obtainable from (or as present in; as derivable from; as obtained or derived from) seeds deposited under accession number NCIMB 42158, or from progeny thereof (e.g. obtained by selfing), for generating spinach plant comprising resistance against at least *Peronospora farinosa* races 7-14 (optionally further against one or more of races 1-6, and/or optionally against UA4712) is provided.

It is noted that also allelism tests can be used to determine whether the resistance gene in a spinach plant is the same gene or a different gene as the RPF11 gene as present in NCIMB42158 (or in progeny thereof). So, NCIMB42158 (or progeny) can be crossed with another spinach plant comprising the same resistance phenotype and in progeny of such a cross one can determine in which ratios the phenotype segregates. Thus, in one aspect a spinach plant is provided comprising resistance against *P. ferinosa* races 7-14, wherein said resistance gene conferring said resistance phenotype is the dominant RPF11 gene as present in NCIMB42158 (or progeny thereof), i.e. is allelic to RPF11 (is a different allele of the RPF11 gene found in NCIMB42158), as determinable in an allelism test. Allelism tests for dominant genes are known in the art and are e.g. described in Hibberd et al. 1987 (Phytopathology 77: 1304-1307).

Seeds

Seeds from which any of the plants of the invention can be grown are provided, as are containers or packages containing or comprising such seeds. Seeds can be distinguished from other seeds due to the presence of the RPF11 resistance gene, either phenotypically (based on plants having the RPF11 resistance phenotype) and/or using molecular methods. Said molecular methods include the use of molecular markers described herein, i.e. SNP_01, SNP_02, a marker in between SNP_01 and SNP_02 linked to the RPF11 gene.

In one aspect, seeds are packaged into small and/or large containers (e.g., bags, cartons, cans, etc.). The seeds may be pelleted prior to packing (to form pills or pellets) and/or treated with various compounds, such as seed coatings.

Seed pelleting can be combined with film coating (Halmer, P. 2000. Commercial seed treatment technology. In: Seed technology and its biological basis. Eds: Black, M. and Bewley, J. D., pages 257-286). Pelleting creates round or rounded shapes, which are easily sown with modern sowing machines. A pelleting mixture typically contains seeds and at least glue and filler material. The latter could be, for example, clay, mica, chalk or cellulose. In addition, certain additives can be included to improve particular properties of the pellet, e.g., a seed treatment formulation comprising at least one insecticidal, acaricidal, nematicidal or fungicidal compound can be added directly into the pelleting mixture or in separate layers. A seed treatment formulation can include one of these types of compounds only, a mixture of two or more of the same type of compounds or a mixture of one or more of the same type of compounds with at least one other insecticide, acaricide, nematicide or fungicide.

Formulations especially suitable for the application as a seed treatment can be added to the seed in the form of a film coating including also the possibility of using the coating in or on a pellet, as well as including the seed treatment formulation directly into the pellet mixture. Characteristically, a film coating is a uniform, dust-free, water permeable film, evenly covering the surface of all individual seeds (Halmer, P. 2000. Commercial seed treatment technology. In: Seed technology and its biological basis. Eds: Black, M. and Bewley, J. D., pages 257-286). Besides the formulation, the coating mixture generally also contains other ingredients such as water, glue (typically a polymer), filler materials, pigments and certain additives to improve particular properties of the coating. Several coatings can be combined on a single seed.

In addition, several combinations with film coating are possible: the film coating can be added on the outside of the pellet, in between two layers of pelleting material, and directly on the seed before the pelleting material is added. Also more than 1 film coating layer can be incorporated in a single pellet. A special type of pelleting is encrusting. This technique uses less filler material, and the result is a 'mini-pellet'.

Seeds may also be primed. Spinach is often primed. Priming is a water-based process that is performed on seeds to increase uniformity of germination and emergence from the soil, and thus enhance vegetable stand establishment. Priming decreases the time span between the emergence of the first and the last seedlings. Methods how to prime spinach seeds are well known in the art (see, e.g., Chen et al. 2010, Seed Sci. & Technol. 38: 45-57).

Plant Parts and Vegetative Reproductions

In a further aspect plant parts, obtained from (obtainable from) a plant of the invention are provided herein, and containers or packages comprising said plant parts.

In a preferred embodiment, the plant parts are leaves of spinach plants of the invention, preferably harvested leaves, or parts of these. Leaves may be loose, bunched, fresh (e.g. in bags), frozen, blanched or boiled. Leaves may be fresh or processed, they may be part of food or feed products, such as salads, etc.

Other plant parts, of plants of the invention, include stems, cuttings, petioles, cotyledons, flowers, anthers, pollen, ovaries, roots, root tips, protoplasts, callus, microspores, stalks, ovules, shoots, seeds, embryos, embryo sacs, cells, meristems, buds etc.

Seeds include for example seeds produced on the plant of the invention after self-pollination or seed produced after cross-pollination, e.g. pollination of a plant of the invention with pollen from another spinach plant or pollination of another spinach plant with pollen of a plant of the invention.

In one aspect, the plant parts or seeds can be identified by the presence of the donor genotype for SNP_01 and/or SNP_02 and/or a molecular marker located in between SNP_01 and SNP_02.

In a further aspect, the plant part is a plant cell. In still a further aspect, the plant part is a non-regenerable cell or a regenerable cell. A non-regenerable cell is a cell which cannot be regenerated into a whole plant through in vitro culture, but the non-regenerable cell may be in a plant or plant part (e.g. leaves) of the invention. In another aspect, the plant cell is a somatic cell.

In a further aspect the plant cell is a reproductive cell, such as an ovule or pollen. These cells are haploid. When they are regenerated into whole plants, they comprise the haploid genome of the starting plant. If chromosome doubling occurs (e.g. through chemical treatment), a double haploid plant can be regenerated. In one aspect the plant of the invention, comprising the RPF11 resistance gene is a haploid or a double haploid spinach plant.

Moreover, there is provided an in vitro cell culture or tissue culture of spinach plants of the invention in which the cell- or tissue culture is derived from a plant parts described above, such as, for example and without limitation, leaves, pollen, embryos, cotyledon, hypocotyls, callus, meristematic cells, roots, root tips, anthers, flowers, seeds or stems, somatic cells, reproductive cells.

Therefore, one aspect provides a cell culture or tissue culture comprising cells or tissues derived from a part a of a spinach plant of the species *Spinacia oleracea* comprising resistance against *Peronospora farinosa* races 7-14, wherein said resistance is conferred by a single dominant gene introgressed from *Spinacia tetrandra* or *Spinacia turkestanica*, which gene is located between SNP_01 at nucleotide 101 of SEQ ID NO: 1 or of a sequence comprising at least 95% sequence identity to SEQ ID NO: 1 and SNP_02 at nucleotide 101 of SEQ ID NO: 2 or of a sequence comprising at least 95% sequence identity to SEQ ID NO: 2.

In one aspect the cells or tissues can be identified by the presence of the donor genotype for SNP_01 and/or SNP_02 and/or a molecular marker located in between SNP_01 and SNP_02.

Also provided are spinach plants regenerated from the above-described plant parts, or regenerated from the above-described cell or tissue cultures, said regenerated plant having a Pfs resistance phenotype (as conferred by the RPF11 gene), i.e. retains the RPF11 gene (or the introgression fragment comprising the RPF11 gene) of the invention. These plants can also be referred to as vegetative propagations of plants of the invention. In one aspect such plants can be identified by the presence of the donor genotype for SNP_01 and/or SNP_02 and/or a molecular marker located in between SNP_01 and SNP_02.

Also provided are harvested leaves of plants of the invention and packages comprising a plurality of leaves of plants of the invention. These leaves thus comprise the RPF11 gene of the invention, detectable by e.g. linked molecular markers or phenotypically (for the originally used whole plant and/or regenerated plant).

The invention also provides for a food or feed product comprising or consisting of a plant part described herein. The food or feed product may be fresh or processed, e.g., canned, steamed, boiled, fried, blanched and/or frozen etc. Examples are salad or salad mixtures comprising leaves or parts of leaves of plants of the invention.

A spinach plant of the invention or a progeny thereof retaining the Pfs resistance phenotype conferred by the RPF11 gene and/or retaining the introgression fragment comprising the RPF11 gene identifiable by the presence of the donor genotype for SNP_01 and/or SNP_02 and/or a molecular marker located in between SNP_01 and SNP_02, e.g. as present in NCIMB 42158, and parts of the afore-mentioned plants, can be suitably packed for, e.g., transport, and/or sold fresh. Such parts encompass any cells, tissues and organs obtainable from the seedlings or plants, such as but not limited to: leaves, cuttings, pollen, parts of leaves, and the like.

Leaves may be harvested immature, as baby-leaf or baby spinach, or mature. A plant, plants or parts thereof may be packed in a container (e.g., bags, cartons, cans, etc.) alone or together with other plants or materials. Parts can be stored and/or processed further. Encompassed are therefore also food or feed products comprising one or more of such parts, such leaves or parts thereof obtainable from a plant of the invention, a progeny thereof and parts of the afore-mentioned plants. For example, containers such as cans, boxes, crates, bags, cartons, Modified Atmosphere Packaging, films (e.g. biodegradable films), etc. comprising plant parts of plants (fresh and/or processed) of the invention are also provided herein.

Plants and Progeny

In another embodiment, plants and parts of spinach plants of the invention, and progeny of spinach plants of the invention are provided, e.g., grown from seeds, produced by sexual or vegetative reproduction, regenerated from the above-described plant parts, or regenerated from cell or tissue culture, in which the reproduced (seed propagated or vegetatively propagated) plant comprises resistance against at least Pfs races 7-14, optionally further against one or more of races 1-6, and/or optionally against UA4712 (Pfs race 15) (as conferred by the RPF11 gene).

In one aspect, a progeny plant of a spinach plant of the invention is a progeny plant that retains the RPF11 resistance gene located between SNP_01 of SEQ ID NO 1 and SNP_02 of SEQ ID NO 2 which gene confers resistance to *Peronospora farinosa* races 7-14.

In another aspect, the progeny plant is a spinach plant of the species *Spinacia oleracea* comprising resistance against *Peronospora farinosa* races 7-14, wherein said resistance is conferred by a single dominant gene introgressed from *Spinacia tetrandra* or *Spinacia turkestanica*, which gene is located between SNP_01 at nucleotide 101 of SEQ ID NO: 1 or of a sequence comprising at least 95% sequence identity to SEQ ID NO: 1 and SNP_02 at nucleotide 101 of SEQ ID NO: 2 or of a sequence comprising at least 95% sequence identity to SEQ ID NO: 2.

Preferably, the presence the RPF11 gene is identifiable by the donor genotype for SNP_01 and/or SNP_02 and/or a molecular marker located in between SNP_01 and SNP_02 and linked to RPF11.

In one aspect, the progeny plant comprises an Adenine for SNP_01 and/or of SNP_02.

As mentioned before, whether or not a plant, progeny or vegetative propagation comprises the Pfs resistance phenotype as conferred by the RPF11 gene can be tested phenotypically using e.g. the Pfs disease resistance assays as described above or in the Examples; and/or using molecular techniques such as molecular marker analysis, DNA sequencing (e.g. whole genome sequencing to identify the wild introgression), chromosome painting, etc.

In one embodiment, the RPF11 resistance gene, e.g. as obtainable from (obtained from; as found in) plants deposited under NCIMB 42158, or progeny thereof, or as obtainable from other wild donors, can be combined with other *Peronospora farinosa* resistance genes or resistance loci (e.g. RPF1-RPF6, R6, etc.) or with other traits, such resistance against bacteria (e.g. *Pseudomonas syringae* pv. *spinacea; Erwinia carotovora*), fungi (e.g. *Albugo occidentalis; Colletotrichum dematium* f. sp. *spinaciae; Stemphylium botryosum* f. sp. *spinacia*), viruses (e.g. viruses causing curly top disease) or nematodes. This can be done by traditional breeding techniques, e.g. by backcrossing in order to introduce one or more traits into a plant of the invention or in order to introduce the RPF11 gene of a plant of the invention into another spinach plant comprising such one or more additional traits. Thus, in one aspect a plant of the invention is used as a donor of the RPF11 gene, while in another aspect a plant of the invention is used as recipient of one or more other traits.

Furthermore, the invention provides for progeny comprising or retaining the Pfs resistance phenotype (conferred by the RPF11 gene), such as progeny obtained by, e.g., selfing one or more times and/or cross-pollinating a plant of the invention with another spinach plant of a different variety or breeding line, or with a spinach plant of the invention one or more times. In particular, the invention provides for progeny that retain the RPF11 gene (conferring the Pfs resistance phenotype), e.g. of (as found in) NCIMB 42158 or as introgressed from other wild donor plants. In one aspect the invention provides for a progeny plant comprising the RPF11 resistance, such as a progeny plant that is produced from a spinach plant comprising the RPF11 resistance by one or more methods selected from the group consisting of: selfing, crossing, mutation, double haploid production or transformation.

Mutation may be spontaneous mutations or human induced mutations or somaclonal mutations.

In one embodiment, plants or seeds of the invention may also be mutated (by e.g. irradiation, chemical mutagenesis, heat treatment, TILLING, etc.) and/or mutated seeds or plants may be selected (e.g. natural variants, somaclonal variants, etc.) in order to change one or more characteristics of the plants. Similarly, plants of the invention may be transformed and regenerated, whereby one or more chimeric genes are introduced into the plants.

Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into the plants, or progeny thereof, by transforming a plant of the invention or progeny thereof with a transgene that confers the desired trait, wherein the transformed plant retains the RPF11 gene and the Pfs resistance phenotype conferred by it and contains the desired trait.

The RPF11 gene or allele may be transferred to progeny by further breeding. In one aspect progeny are $F_1$ progeny obtained by crossing a plant of the invention with another plant or 51 progeny obtained by selfing a plant of the invention. Also encompassed are F2 progeny obtained by selfing the $F_1$ plants, or further generation progeny. "Further breeding" encompasses traditional breeding techniques (e.g., selfing, crossing, backcrossing), marker assisted breeding, and/or mutation breeding. In one embodiment, the progeny have the Pfs resistance phenotype of e.g. NCIMB 42158 and comprising the RPF11 gene (or introgression comprising the gene or the reduced size introgression fragment comprising the RPF11 gene) obtainable/obtained from (or as found in) e.g. NCIMB 42158 or as introgressed from other wild donor plants.

In one aspect, haploid plants and/or double haploid plants of plant of the invention are encompassed herein, which comprise resistance against at least *Peronospora farinosa* races 7-14 (optionally further against one or more of races 1-6, and/or optionally against UA4712), as conferred by the RPF11 gene or by the introgression fragment comprising the RPF11 gene. Haploid and double haploid (DH) plants can for example be produced by anther or microspore culture and regeneration into a whole plant. For DH production chromosome doubling may be induced using known methods, such as colchicine treatment or the like. So, in one aspect a spinach plant is provided, comprising Pfs resistance phenotype as described, wherein the plant is a double haploid plant.

In another embodiment, the invention relates to a method for producing spinach seed, comprising crossing a plant of the invention with itself or a different spinach plant and harvesting the resulting seed. In a further embodiment the invention relates to seed produced according to this method and/or a spinach plant produced by growing such seed. Thus, a plant of the invention may be used as male and/or female parent, in the production of spinach seeds, whereby the plants grown from said seeds comprise at least *Peronospora farinosa* races 7-14 (optionally further against one or more of races 1-6, and/or optionally against UA4712), due to the presence of the RPF11 gene.

Thus, in one aspect, progeny of a spinach plant of the invention are provided, wherein the progeny plant is produced by selfing, crossing, mutation, double haploid production or transformation and wherein the progeny retain the RPF11 resistance gene (and phenotype conferred by it) described herein, i.e. obtainable by crossing a spinach plant, grown from seeds e.g. deposited under accession number NCIMB 42158 or a plant comprising the RPF11 gene introgressed from another wild donor plant, with another spinach plant. In other words, the resistance gene or locus (or introgression fragment comprising the gene or locus) as present in/found in/as derived from (or as derivable from) e.g. seed deposit NCIMB 42158 or as introgressed from other wild donor plants is retained in the progeny plants.

Molecular markers may also be used to aid in the identification of the plants (or plant parts or nucleic acids obtained therefrom) containing the RPF11 resistance gene or locus or allele(s). For example, one can develop one or more suitable molecular markers which are closely genetically (and preferably also physically) linked to the RPF11 resistance gene, locus or allele. This can be done by crossing a resistant spinach plant (comprising RPF11) with a susceptible spinach plant and developing a segregating population (e.g. F2 or backcross population) from that cross. The segregating population can then be phenotyped for Pfs resistance and genotyped using e.g. molecular markers such as SNPs (Single Nucleotide Polymorphisms), AFLPs (Amplified Fragment Length Polymorphisms; see, e.g., EP 534 858), or others, and by software analysis molecular markers which co-segregate with the Pfs resistance trait in the segregating population can be identified and their order and genetic distance (centimorgan distance, cM) to the RPF11 resistance gene or locus can be identified. Molecular markers which are closely linked to RPF11 resistance locus, e.g. markers at a 5 cM distance or less, can then be used in detecting and/or selecting plants (e.g. plants of the invention or progeny of a plant of the invention) or plant parts comprising or retaining the introgression fragment comprising the RPF11 resistance gene or locus. Such closely linked molecular markers can replace phenotypic selection (or be used in addition to phenotypic selection) in breeding programs, i.e. in Marker Assisted Selection (MAS). Preferably flanking markers are used in MAS, i.e. one marker on either side of the RPF11 gene or locus, e.g. SNP_01 and SNP_02, but also other flanking markers may be used.

Any other type of molecular marker and/or other assay that is able to identify the relative presence or absence of a trait of interest (i.e. the RPF11 gene or locus) in a plant or plant part can also be useful for breeding purposes.

Deposit Information

A total of 2500 seeds of spinach NCIMB 42158 were deposited by Nunhems B. V. on 10 Sep. 2013, at the NCIMB Ltd., Ferguson Building, Craib stone Estate, Bucksburn, Aberdeen AB21 9YA, United Kingdom (NCIMB). Access to the deposit will be available during the pendency of this application to persons determined by the Director of the U.S. Patent Office to be entitled thereto upon request. Subject to 37 C.F.R. § 1.808 (b), all restrictions imposed by the depositor on the availability to the public of the deposited material will be irrevocably removed upon the granting of the patent. The deposit will be maintained for a period of 30 years, or 5 years after the most recent request or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in plant breeding, chemistry, biology, plant pathology or related fields are intended to be within the scope of the following claims.

The present invention will be further illustrated in the following Examples which are given for illustration purposes only and are not intended to limit the invention in any way.

EXAMPLES

Example 1

Pfs Resistance Phenotype of Spinach Comprising the RPF11 Gene

The resistance to downy mildew infection was assayed with the help of a differential set obtained from the Naktuinbouw.

Spinach plants of the invention (comprising the RPF11 gene) were planted along with spinach plants from different other genotypes (see Table 1) in trays containing BVB substrate (Euroveen, Grubbenvorst), and covered with Agravermiculite (Pull, Rhenen). Per test at least 10 plants from one genotype where tested in one or two replications. The trays were placed in a climate cell at 12° C./15° C. (day/night) with a 12 h photoperiod. Plants were inoculated by spraying a sporangial suspension ($2.5 \times 10^5$/ml) of a pathogenic race of *Peronospora farinosa* f. sp. *spinaciae* 14 days after seeding. In this manner pathogenic races were assayed (as shown in Table 2).

The inoculated plants were covered with transparent plastic material with 100% relative humidity for a 24 h period, after this period the plastic was removed on top to lower the relative humidity to 80%.

After 10 days, the plants were scored as 'resistant' or 'susceptible' based on symptoms of pathogen sporulation on the cotyledons and true leaves, as described by Irish et al. (2007; Plant Dis. 91: 1392-1396). Plants exhibiting any evidence of sporulation were considered 'susceptible'. Plants not exhibiting sporulation were considered 'resistant'. Resistant plants were re-inoculated to assess whether plants initially scored as resistant had escaped infection, or whether they were truly resistant. These plants were scored again 10 days after the second inoculation.

Any genotype with <15% of plants being categorized as 'susceptible' (i.e. with >85% of plants categorized as resistant) were considered as a resistant genotype.

Normally the resistance of a spinach hybrid is the effect of two genes, as described by Handke et al. (2000; Gartenbauwissenschaft, 65: 73-78). For example in the hybrid Andromeda, the RPF2 resistance gene (Lazio type, resistance against Pfs races) is combined with a RPF3 (Califlay type, resistance against Pfs races 1, 3, 5, 8, 9, 11, 12, and 14) resistance gene. This combination of genes results in resistance to Pfs races 1-12, and 14 and susceptibility to Pfs race 13 (see Table 2). The new resistance gene, RPF11, gave resistance to all tested races. The resistance works both homozygous in fixed lines as in heterozygous backgrounds, like spinach hybrids (see Table 3).

The RPF11 resistance trait of the present invention is conferred by a single dominant resistance gene, which has the great advantage that the RPF11 resistance trait can be easily transferred into other spinach lines or varieties by crossing/introgression, and that it can easily be combined with other resistance genes. The RPF11 gene confers resistance to the tested Pfs races, especially races Pfs 7-14, without the need to use a complimentary resistance gene.

a successful infection by the fungus is visible as sporulation on the cotyledon or leaf. Resistance (indicated as "−" in the table) is the absence of sporulation on the cotyledons and mature leaves. "(−)" indicates reduced level of infection, often referred to as field resistance=sparse sporulation on the tips of cotyledons. "+/−" indicates variability in the number of resistant and susceptible plants observed. *In WO2013/064436 the R6 gene is described as conferring resistance against Pfs1-6, Pfs9, Pfs11, Pfs12, Pfs13 and Pfs14 (UA4410).

Example 2

Introduction of the RPF11 Resistance Trait into Other Spinach Plants

A plant of the invention was crossed (as a father) with a plant that does not contain the RPF11 resistance gene, to obtain an F1. Thirty plants of the F1 population were tested for resistance to Pfs races 11, 12, 13, and 14 described in Example 1. This particular resistance was absent from the mother plant used in the said cross. All 40 plants showed the resistance pattern of the invention, i.e. resistance to Pfs races 11, 12, 13, and 14. This demonstrated that the RPF11 resistance gene inherits in a dominant manner.

In another experiment, a plant of the invention was crossed (as a mother) with a different spinach plant susceptible to all known races. Plants of the F1 population were selfed, and a total of 1115 plants of the F2 generation were tested for Pfs resistance, as described in Example 1.

It was observed that resistance against Pfs races 2, 5, 10, 11, 12, 13, 14, and UA4712 (synonym Pfs race 15) segregated in the F2 generation in a fashion that corresponds to dominant monogenic inheritance: 835 of the 1115 F2 plants exhibited the RPF11-resistance phenotype. Table 3 gives a detailed overview of the segregation of the RPF11 resistance

TABLE 2

| Variety | Pfs7 | Pfs8 | Pfs9 | Pfs10 | Pfs11 | Pfs12 | Pfs13 | Pfs14 | UA4712 |
|---|---|---|---|---|---|---|---|---|---|
| Viroflay | + | + | + | + | + | + | + | + | + |
| Resistoflay | + | + | + | + | + | + | + | + | + |
| Califlay | + | − | − | + | − | − | + | − | + |
| Clermont | + | + | + | + | + | + | + | + | − |
| Campania | − | + | + | + | − | + | +/− | + | − |
| Boeing (=Avenger in USA) | − | + | − | + | − | + | − | + | − |
| Lion | − | − | − | + | − | − | − | − | − |
| Lazio | − | − | − | − | + | + | + | + | − |
| Whale | (−) | − | − | + | − | − | + | (−) | + |
| Polka | + | − | − | + | − | − | + | − | + |
| Pigeon | − | − | − | − | − | − | − | + | + |
| R6 (data from WO2013/064436*) | + | + | − | + | − | − | − | − | |
| Andromeda F1 (US2012/0222147) | − | − | − | − | − | − | + | − | − |
| Parent 1 of Andromeda | + | − | − | + | − | − | + | − | + |
| Parent 2 of Andromeda | − | − | − | − | + | + | + | + | − |
| NCIMB 42158 (RPF11) | − | − | − | − | − | − | − | − | − |

Table 2 shows the differential set of spinach downy mildew races and the resistance of various spinach varieties (hybrids) to each one of these pathogenic races. A susceptible reaction (indicated as "+" in the table) is scored when gene in eight Pfs assays. Chi-square tests confirmed that the observed segregation in the F2 populations was consistent with a 3:1 (resistant:susceptible) segregation of the RPF11 resistance profile.

TABLE 3

| Outcome | Race | | | | | | | | |
|---|---|---|---|---|---|---|---|---|---|
| | Pfs2 | Pfs5 | Pfs10 | Pfs11 | Pfs12 | Pfs13 | Pfs14 | UA4712 | Total |
| Resistant | 86 (80%) | 87 (76%) | 162 (76%) | 68 (65%) | 81 (76%) | 159 (74%) | 87 (80) | 105 (71%) | 835 (75%) |
| Susceptible | 22 (20%) | 27 (24%) | 50 (24%) | 36 (35%) | 25 (24%) | 55 (26%) | 22 (20%) | 43 (29%) | 280 (25%) |
| Total observations | 108 | 114 | 212 | 104 | 106 | 214 | 109 | 148 | 1115 |
| Chi square probablity | 0.267 | 0.746 | 0.634 | 0.0235 | 0.737 | 0.813 | 0.245 | 0.255 | 0.931 |
| Fitting the expected segregation pattern (p > 0.05) | yes | yes | yes | yes | yes | yes | yes | yes | yes |

Table 3: Overview of segregation of the RPF11 resistance profile in eight Pfs assays, expressed in the number and percentage of plants observed as resistant or susceptible per Pfs race. The plant belong to the progeny of an inbred from a cross between a spinach plant which lacks the RPF11 gene and a genotype of the invention containing the RPF11 gene. Chi-square tests confirm that the results fit the expected segregation pattern for a dominant monogenic trait. In all cases chi-square values are well above 0.05.

Similar segregation results were obtained when the progeny of a cross between a plant that carries the RPF11 resistance gene and a plant not carrying the said gene were assayed for other Pfs races.

Example 3

Mapping of Resistance Gene RPF11

A F2 population was developed by crossing spinach plants of the invention, containing RPF11, with a spinach plant that does not contain the RPF11 resistance gene. Linkage mapping was conducted, and Single Nucleotide Polymorphism markers (SNPs) SNP_01 and SNP_02 shown in Table 4 were identified flanking the RPF11 gene.

TABLE 4

SNP markers flanking the RPF11 gene

| SNP and nucleotide position (nt) in the sequence | SNP genotype in spinach plant comprising the donor fragment in homozygous form | SNP genotype in spinach plant comprising the donor fragment in heterozygous form | SNP genotype of the recurrent parent, lacking the introgression fragment | SNP marker sequence |
|---|---|---|---|---|
| SNP_01 at nt 101 | AA | AG | GG | ATTCTAAATCAATTTATTT GTGTATTCATTCTTTTGTA TTAACAGAGACTATTTCAA AGTAAGATTATTCATTAAT TAATTATTGCTTCTTACTT CCACC[A/G]TTTCAAAAAA AATTGCTAACAATTTTAAT TTTGTCATTATTCATACAC CAACTTTGACCATATATTT TATGGCATGTAGAAACTCT TACTTCCACCATTT (SEQ ID NO: 1) |
| SNP_02 at nt 101 | AA | AC | CC | TCATTAATTTCATTTTCTT GTCGTATACGATTTAAATC GTTTTGTCATGTATTGTTA GCCTTTTGTATTGCATATA TTGCTTGCATTAACTTTCA CATTA[C/A]TGCGGAAATT TTAATAAGAAACTAAAGT AAAAACATGCATAATATT GCTTGAAAACTCTTTGAAA TATGATTAACACTTTTGAA ATTAATTTGATAACTA (SEQ ID NO: 2) |

The invention claimed is:

1. A spinach plant of the species *Spinacia oleracea* comprising resistance against *Peronospora farinosa* races 7-14, wherein said resistance is conferred by an introgression fragment comprising a single dominant gene, said introgression fragment comprising an Adenine for SNP_02 for nucleotide 101 of SEQ ID NO: 2, and an Adenine for SNP_01 for nucleotide 101 of SEQ ID NO: 1; wherein said gene is the gene present in plants grown from seeds, a representative sample of seeds having been deposited under accession number NCIMB 42158.

2. The plant according to claim 1, wherein the gene further confers resistance against *Peronospora farinosa* races 1, 2, 3, 5 and 6.

3. The plant according to claim 1, wherein the gene further confers resistance against *Peronospora farinosa* race 15.

4. The spinach plant according to claim 1, wherein the gene is located between SNP_01 at nucleotide 101 of SEQ ID NO: 1 and SNP_02 at nucleotide 101 of SEQ ID NO: 2.

5. The plant according to claim 1, wherein said spinach plant is a hybrid plant.

6. The plant according to claim 1, wherein said spinach plant is an inbred plant.

7. The plant according to claim 1, wherein the spinach plant is savoy, semi-savoy, or smooth leaved.

8. The plant according to claim 1, wherein said resistance against *Peronospora farinosa* is conferred by an introgression fragment from *Spinacia turkestanica*.

9. The plant according to claim 8, wherein said introgression fragment is the fragment present in spinach seeds, a representative sample of seeds having been deposited under accession number NCIMB 42158, or a sub-fragment thereof.

10. A seed from which the plant according to claim 1 can be grown.

11. A leaf of the plant according claim 1.

12. A progeny plant of the spinach plant according to claim 1, wherein said progeny plant retains the introgression fragment comprising the resistance gene and comprising an Adenine for SNP_02 for nucleotide 101 of SEQ ID NO: 2 and an Adenine for SNP_01 for nucleotide 101 of SEQ ID NO: 1; which gene confers resistance to *Peronospora farinosa* races 7-14.

13. The progeny plant according to claim 12, wherein said progeny plant is resistant against *Peronospora farinosa* races 7-14 and race 15.

14. The progeny plant according to claim 12, wherein the progeny plant is produced by one or more of selfing, crossing, mutation, double haploid production and/or transformation.

15. A part of the spinach plant according to claim 1, wherein the part is a stem, a cutting, a petiole, a cotyledon, a flower, an anther, a pollen, an ovary, a root, a root tip, a protoplast, a callus, a microspore, a stalk, an ovule, a shoot, a seed, an embryo, an embryo sac, a cell, a meristem, a bud or a leaf, and wherein said part comprises said introgression fragment.

16. A cell culture or tissue culture comprising cells or tissues derived from a part of a spinach plant of the species *Spinacia oleracea* comprising resistance against *Peronospora farinosa* races 7-14, wherein said resistance is conferred by an introgression fragment comprising a single dominant gene wherein said resistance gene is the gene present in plants grown from seeds, a representative sample of seeds having been deposited under accession number NCIMB 42158 and said introgression fragment comprises an Adenine for SNP_02 at nucleotide 101 of SEQ ID NO: 2, and an Adenine for SNP_01 for nucleotide 101 of SEQ ID NO: 1; and wherein said cells or tissues comprise said introgression fragment.

17. A spinach plant regenerated from the cell culture or tissue culture of claim 16, and comprising resistance against *Peronospora farinosa* races 7-14 and comprising said introgression fragment.

18. A method for generating a spinach plant comprising resistance against *Peronospora farinosa* races 7-14 comprising:

a) crossing a first spinach plant of the species *Spinacia oleracea* that comprises resistance against *Perono-*

*spora farinosa* races 7-14 with a second spinach plant that is susceptible against one or more of *Peronospora farinosa* races 7 to 14, wherein said resistance is conferred by an introgression fragment comprising a single dominant gene, and wherein said gene is the gene present in plants grown from seeds, a representative sample of seeds having been deposited under accession number NCIMB 42158 and wherein said introgression fragment comprises an Adenine for SNP_02 at nucleotide 101 of SEQ ID NO: 2; an Adenine for SNP_01 at nucleotide 101 of SEQ ID NO: 1; and b) growing a progeny plant from said crossing, wherein said progeny plant comprises said single gene.

19. The method of claim 18, further comprising c) selfing a plant grown from progeny of said crossing, one or more times to produce a further generation selfing progeny and/or backcrossing a plant grown from progeny of said crossing or grown from the further generation selfing progeny with a spinach plant is susceptible against one or more of *Peronospora farinose* races 7 to 14; and d) identifying a spinach plant among the progeny plants of step c) that comprises said single dominant gene of the first parent plant of step a).

20. A spinach plant obtained by the method of claim 19, said spinach plant comprising resistance against *Peronospora farinosa* races 7-14 and comprising said introgression fragment.

21. The method according to claim 19, wherein the introgression fragment further comprises an Adenine for SNP_01 at nucleotide 101 of SEQ ID NO: 1.

22. The method according to claim 19, wherein the genotype of SNP_02 is used to identify a plant in step d).

\* \* \* \* \*